(12) United States Patent
Takaoka

(10) Patent No.: US 6,496,267 B1
(45) Date of Patent: Dec. 17, 2002

(54) SCANNING MICROSCOPE

(75) Inventor: Hideyuki Takaoka, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/541,914

(22) Filed: Apr. 3, 2000

(30) Foreign Application Priority Data

Apr. 5, 1999 (JP) .......................................... 11-097302

(51) Int. Cl.[7] .............................................. G01N 21/64
(52) U.S. Cl. ...................... 356/497; 356/72; 356/73.1; 356/317; 356/318; 356/417; 356/484; 356/485; 356/490; 356/497; 250/227.7
(58) Field of Search ........................ 356/73.1, 72, 484, 356/485, 490, 497, 317, 318, 417; 250/227.7

(56) References Cited

U.S. PATENT DOCUMENTS

| 5,321,501 A | 6/1994 | Swanson et al. | |
| 6,404,545 B1 * | 6/2002 | Ishiwata | ..................... 359/235 |

FOREIGN PATENT DOCUMENTS

| JP | 11-119106 | 4/1999 |

OTHER PUBLICATIONS

Journal of Modern Optics, 1998, vol. 45, No. 4, pp. 765–775, Low–coherence fibre heterodyne interferometer for both dc and high–frequency vibration measurements in the inner ear. Ernst Dalhoff et al.

* cited by examiner

*Primary Examiner*—John R. Lee
*Assistant Examiner*—Zia R. Hashmi
(74) *Attorney, Agent, or Firm*—Pillsbury Winthrop LLP

(57) ABSTRACT

A scanning microscope allowing fluorescence observation and morphological observation to be simultaneously performed on the same region of interest and permitting both a fluorescence observation image and a morphological observation image to be obtained within a reduced period of time. The scanning microscope includes a device for splitting low-coherence light from a low-coherence light source between a first optical path and a second optical path. A frequency modulator is placed in at least one of the first and second optical paths to produce a frequency difference between light passing through the two optical paths. An objective optical system is placed in the first optical path to apply light to a sample and to collect light from the sample. A scanning device is placed in the first optical path to scan the sample and the light applied by the objective optical system relative to each other in a plane perpendicular to the optical axis. A combining device combines together the first and second optical paths. An interference signal detecting system detects an interference signal having the frequency difference from the combined light. A fluorescence branching device branches fluorescence from the sample excited by the low-coherence light. A fluorescence detecting system detects the branched fluorescence.

24 Claims, 10 Drawing Sheets

SCANNING MICROSCOPE

BACKGROUND OF THE INVENTION

The present invention relates to scanning microscopes. More particularly, the present invention relates to a scanning microscope which allows morphological observation and fluorescence observation to be performed simultaneously and enables both a morphological observation image and a fluorescence observation image to be obtained within a reduced period of time.

A technique called "low-coherence interferometry" such as that disclosed in U.S. Pat. No. 5,321,501 is known as a method that allows observation of the inside of an opaque scattering sample, e.g. a biological tissue. FIG. 11 shows a typical optical system for the low-coherence interferometry. Light from a light source 81 with a short coherence length is split by a beam splitter 82 between a signal light path leading to a sample 5 and a reference light path leading to a reflecting mirror 83. Light going and returning along the signal light path and the reference light path are recombined in the beam splitter 82. At this time, because the signal light path forms an optical path length substantially equal to that of the reference light path at an observation position 6 within the sample 5, only light scattered back from a region at the observation position 6 within a range in the optical axis direction that is substantially equal to the coherence length interferes with the reference light. Accordingly, by detecting the resulting interference signal with a detector 84, information about the inside of the sample 5 can be selectively obtained in the optical axis direction. In general, the reflecting mirror 83 in the reference light path is moved in the optical axis direction, thereby performing scanning in the direction of depth of the sample and, at the same time, giving a Doppler shift to the reference light. The low-coherence interferometry generally includes heterodyne interferometric measurement that is carried out to detect a beat signal having a Doppler shift frequency in the interference signal. Therefore, the measurement can be performed with a very high S/N ratio. Accordingly, if near infrared light or the like is used as the light source 81, it is possible to detect feeble scattered light from a position as deep as several millimeters from the surface of the scattering sample 5. By scanning the signal light or the sample 5 in a plane perpendicular to the optical axis, it is possible to obtain an image of a section perpendicular to the optical axis.

Meanwhile, a low-coherence interferometric method is published in "Journal of Modern Optics", Vol. 45, No. 4, p.765 (1998), in which acoustooptic devices are disposed in the signal light path and the reference light path, respectively, and a beat signal corresponding to the difference between the modulation frequencies of the acoustooptic devices is detected without moving the reflecting mirror.

Incidentally, a fluorescence observation method is known as an observation method for biological samples or the like. According to the fluorescence observation method, a cellular tissue or a specific substance is labeled with a fluorescent dye, and a fluorescence image produced when excitation light is applied to the sample is observed. The sample may be sliced for microscopic observation. Recently, however, there have been increasing needs to observe biological samples or the like in a living state, and there has been a growing demand for obtaining a fluorescence image at some depths from the sample surface.

During fluorescence observation, it is desirable to be possible to simultaneously obtain morphological information about a fluorescence-labeled tissue or substance and information concerning a surrounding spatial structure. However, it is difficult to obtain information about the inside of a thick sample in ordinary microscopic observation. In observation of such morphological information, for example, when it is intended to observe changes of biological activities of a living biological tissue with time, it is desirable that the time required for the observation should be as short as possible. When morphological observation or the like is performed simultaneously with fluorescence observation, if excitation light is continuously applied to the fluorescence-labeled sample for a long period of time, the fluorescent dye fades. Consequently, the fluorescence image becomes dark as time goes by. Therefore, in this case also, the time required for observation should be minimized.

The above-described patent and literature give no description of a fluorescence observation method and do not mention an arrangement in which low-coherence interferometric measurement is carried out during fluorescence observation. Such an arrangement is disclosed in U.S. patent application Ser. No. 09/172,676 and Japanese Patent Application Unexamined Publication (KOKAI) No. 11-119106, which were filed by the present applicant. However, the disclosed arrangement uses a method in which the reflecting mirror in the reference light path is moved to perform observation. Therefore, it is necessary to move the reflecting mirror also when observing a section within the sample that is perpendicular to the optical axis. Accordingly, when low-coherence interferometric measurement is carried out simultaneously with fluorescence microscopic observation, in which, generally, a section perpendicular to the optical axis is observed, the time required for measurement undesirably lengthens by an amount corresponding to the time needed for mechanical drive of the reflecting mirror.

SUMMARY OF THE INVENTION

In view of the above-described problems with the prior art, an object of the present invention is to provide a scanning microscope in which when performing fluorescence observation of the inside of a thick sample or the inside of an opaque scattering sample, it is possible to simultaneously perform morphological observation for obtaining morphological information or the like in the same region of interest as that for the fluorescence observation, and it is possible to obtain both a fluorescence observation image and a morphological observation image within a reduced period of time.

To attain the above-described object, the present invention provides a scanning microscope including a low-coherence light source and a device for splitting low-coherence light from the low-coherence light source between a first optical path and a second optical path. A frequency modulator is placed in at least one of the first and second optical paths to produce a frequency difference between light passing through the first optical path and light passing through the second optical path without changing the optical path length of each optical path. An objective optical system is placed in the first optical path to apply light to a sample and to collect light from the sample. A scanning device is placed in the first optical path to scan the sample and the light applied by the objective optical system relative to each other in a plane perpendicular to the optical axis of the objective optical system. The scanning microscope further includes a device for combining together the first and second optical paths, and an interference signal detecting system for detecting an interference signal having the frequency difference from the combined light. A fluorescence branching device branches fluorescence from the sample excited by the low-coherence light. A fluorescence detecting system detects the fluorescence branched by the fluorescence branching device.

The arrangement and operation of the scanning microscope according to the present invention will be described below with reference to FIG. 1, which shows the arrangement of the scanning microscope according to the present invention.

Low-coherence light from a low-coherence light source 1 is split between a first optical path and a second optical path by an optical path splitting device 2. In FIG. 1, an optical path along which light reflected by the optical path splitting device 2 travels is defined as a first optical path, and an optical path along which light passing through the optical path splitting device 2 travels is defined as a second optical path. Frequency modulators 3a and 3b are placed in the respective optical paths. The frequency modulators 3a and 3b have been set to produce a frequency difference f between light passing through the first optical path and light passing through the second optical path without changing the optical path length of each optical path. The arrangement may be such that a frequency modulator is provided in only either one of the first and second optical paths. The light passing through the first optical path is applied to a sample 5 through an objective optical system 4. Light reflected and scattered by the sample 5 passes through the objective optical system 4 again. Then, the light is combined with the light passing through the second optical path by devices 7 and 8 for combining the first and second optical paths and led to an interference signal detecting system 9. The interference signal detecting system 9 extracts a beat signal of frequency f from the detected signal. The amplitude of the beat signal is determined to be scattered light intensity information. In the light scattered from the inside of the sample 5, light from the vicinity of an observation position 6 in the sample 5, at which the first optical path has an optical path length substantially equal to that of the second optical path, interferes with the light passing through the second optical path. The above-described vicinity of the observation position 6 is within a range in the optical axis direction that is substantially equal to the coherence length of the low-coherence light source 1. Accordingly, scattered light intensity information in the sample 5 can be obtained with z-resolution substantially equal to the coherence length.

If a fluorescence label excitable by light from the low-coherence light source 1 has been introduced into the sample 5, it is possible to perform fluorescence observation of a specific tissue, substance, etc. in the sample 5. It is not necessary to introduce a fluorescence label when a tissue of interest fluoresces by itself to the wavelength of light from the low-coherence light source 1. Fluorescence emitted from the sample 5 is separated from the low-coherence light by a fluorescence branching device 10 and led to a fluorescence detecting system 11.

Accordingly, the same region 6 in the sample 5 can be observed simultaneously by both the low-coherence interferometric observation method and the fluorescence observation method. In addition, an image of a section in the sample 5 that is perpendicular to the optical axis can be obtained by scanning the light applied to the sample 5 by the objective optical system 4 in a plane (xy-section in FIG. 1) perpendicular to the optical axis of the objective optical system 4 by using a scanning device 12. The sample 5 may be scanned instead of scanning the light applied to the sample 5 by the objective optical system 4.

In the arrangement shown in FIG. 11, even when one point in an xy-section of the sample 5 is observed, the optical path length of the reference light path is changed to produce a frequency difference between the reference light path and the signal light path while scanning the sample 5 in the z-direction. The frequency modulators 3a and 3b in the present invention do not change the optical path lengths of the first and second optical paths. Therefore, observation of one point in an xy-section needs no mechanical drive. In the scanning microscope according to the present invention, there is always a frequency difference f between the first optical path and the second optical path. Accordingly, it is possible to obtain a low-coherence interferometric image of an xy-section at a much higher speed than in the case of the arrangement shown in FIG. 11.

The low-coherence light source 1 may be a pulse laser. In this case, the fluorescence dye can be subjected to multiphoton excitation by the pulse laser. In multiphoton excitation, only the fluorescence dye near the condensed excitation light spot is excited, and no fluorescence is emitted from a region away from the observation plane even if it is irradiated with the excitation light. Therefore, excess background light is suppressed, and the S/N ratio of fluorescence observation is increased.

The fluorescence branching device 10 may be a dichroic mirror. Optimally setting the reflection-transmission characteristics of the dichroic mirror allows efficient separation of fluorescence and scattered light from the sample 5 and thus makes it possible to improve the efficiency of detection of fluorescence and scattered light.

In addition, the present invention provides another scanning microscope including a low-coherence light source and a device for splitting low-coherence light from the low-coherence light source between a first optical path and a second optical path. A frequency modulator is placed in at least one of the first and second optical paths to produce a frequency difference between light passing through the first optical path and light passing through the second optical path without changing the optical path length of each optical path. An objective optical system is placed in the first optical path to apply light to a sample and to collect light from the sample. A scanning device is placed in the first optical path to scan the sample and the light applied by the objective optical system relative to each other in a plane perpendicular to the optical axis of the objective optical system. The scanning microscope further includes a device for combining together the first and second optical paths, and an interference signal detecting system for detecting an interference signal having the frequency difference from the combined light. Further, the scanning microscope includes a fluorescence excitation light source, and an excitation light combining device for combining together excitation light from the fluorescence excitation light source and the low-coherence light in the first optical path. A fluorescence branching device branches fluorescence from the sample excited by the excitation light. A fluorescence detecting system detects the fluorescence branched by the fluorescence branching device.

The arrangement and operation of the second scanning microscope according to the present invention will be described below with reference to FIGS. 2 and 3, which show the arrangement of the second scanning microscope according to the present invention.

The second scanning microscope is similar to the scanning microscope shown in FIG. 1 in the arrangement of a part in which light from a low-coherence light source 1 is split between two optical paths by an optical path splitting device 2, and a beat signal having a frequency difference produced by frequency modulators 3a and 3b is detected by an interference signal detecting system 9. Therefore, a description of this part is omitted. The arrangement shown in FIG. 2 differs from the arrangement shown in FIG. 1 in that the scanning microscope has a fluorescence excitation light source 15 in addition to the low-coherence light source 1. In FIG. 2, excitation light from the fluorescence excitation light source 15 is combined with low-coherence light in the first optical path by an excitation light combining device 16 and applied to a sample 5, together with the low-coherence light. Fluorescence emitted from the sample 5 is separated by a fluorescence branching device 17 and led to a fluorescence detecting system 11. The excitation light combining device and the fluorescence branching device may be arranged to perform each other's function as well as their own functions, as shown by reference numerals 18 and 19 in FIG. 3. That is, in FIG. 3, both the devices 18 and 19 are excitation light combining devices and also fluorescence branching devices.

In the present invention, the scanning microscope has the fluorescence excitation light source 15 separately from the low-coherence light source 1. Therefore, it is possible to select light sources of wavelengths that are most suitable for low-coherence interferometric observation and fluorescence observation, respectively.

The second scanning microscope according to the present invention also allows the same region 6 in the sample 5 to be observed simultaneously by both the low-coherence interferometric observation method and the fluorescence observation method as in the case of the scanning microscope shown in FIG. 1. In addition, an image of an xy-section can be obtained by the scanning device 12, and thus high-speed two-dimensional image observation can be performed.

The excitation light combining device and the fluorescence branching device can be formed from at least two dichroic mirrors. Thus, low-coherence light and fluorescence can be separated from each other efficiently.

The arrangement may be such that one of the excitation light combining device and the fluorescence branching device is a dichroic mirror, and the other is a mirror capable of switching between optical paths. For example, the scanning microscope shown in FIG. 2 may be arranged such that the device denoted by reference numeral 16 is a mirror capable of switching between optical paths, and the device denoted by reference numeral 17 is a dichroic mirror. When, as shown in FIG. 2, the device 16 is placed as a mirror in the first optical path, only fluorescence observation is performed. When both the devices 16 and 17 are withdrawn from the first optical path, only low-coherence interferometric observation is performed. With this arrangement, it is possible to switch between fluorescence observation and low-coherence interferometric observation. This is useful when scattered light and fluorescence from the sample 5 are feeble and it is therefore desired to minimize the loss of light quantity. In FIG. 3, the same action can be obtained by using a mirror capable of switching between optical paths as the device denoted by reference numeral 19 and further using a dichroic mirror as the device denoted by reference numeral 18.

The frequency modulators used in the above-described scanning microscopes according to the present invention may be acoustooptic devices. Acoustooptic devices can readily produce frequency modulation in accordance with the driving frequency thereof and are therefore suitable for the heterodyne measurement in low-coherence interferometry.

In the foregoing scanning microscopes according to the present invention, at least one of the interference signal detecting system and the fluorescence detecting system may be arranged in the form of a confocal system. For example, pinholes or the like are placed on the illumination side and immediately in front of each detecting system, respectively, to form a confocal detecting system. Thus, it is possible to increase the spatial resolution in either or both of low-coherence interferometric observation and fluorescence observation.

In the foregoing scanning microscopes according to the present invention, at least one of the first and second optical paths may be provided with at least one dispersion adjusting device for substantially equalizing dispersion characteristics produced in the first and second optical paths, respectively, in the wavelength region of the above-described low-coherence light. Because low-coherence light has a spectral width of certain size, when it passes through each optical device provided in the optical paths, the optical path length of the light differs for different wavelengths according to the dispersion characteristics of each optical device. For example, if the spectral distribution of the low-coherence light source 1 is as shown in FIG. 12, when light from the low-coherence light source 1 passes through an optical device having dispersion characteristics as shown in FIG. 13, the optical path length of light of $\lambda_l$ shown in FIG. 13 becomes longer than the optical path length of light of $\lambda_h$. In the scanning microscope according to the present invention, low-coherence light split between the first optical path and the second optical path is affected by the dispersion of each optical device in each optical path before being recombined. If the first and second optical paths are different in dispersion characteristics from each other, the difference in optical path length between the first and second optical paths undesirably varies according to wavelengths. Even if the same optical devices are used in the first and second optical paths, when the sample 5 itself has dispersion, the difference in optical path length between the first optical path, which passes through a part of the sample 5, and the second optical path, which does not pass through any part of the sample 5, varies according to wavelengths, undesirably. If the optical path length difference varies according to wavelengths, the observation position 6 in the sample 5 where an interference signal is detected in FIG. 1, for example, varies in the z-axis direction according to wavelengths. Consequently, the resolution and the S/N ratio degrade unavoidably.

Therefore, in the scanning microscopes according to the present invention, at least one of the first and second optical paths is provided with at least one dispersion adjusting device for substantially equalizing dispersion characteristics produced in the first and second optical paths, respectively, in the wavelength region of the low-coherence light, thereby solving the above-described problem.

The at least one dispersion adjusting device provided in the second optical path may be variable in optical thickness. For example, to observe images of sections (in the xy-plane) perpendicular to the optical axis successively in the direction of depth of the sample in order to obtain information concerning a three-dimensional structure inside the sample 5, after each observation of an image in the xy-plane, either the objective optical system 4 or the sample 5 is moved in the z-direction. At this time, the optical path length of the first optical path changes. Therefore, it is necessary to change the optical path length of the second optical path in accordance with the change in optical path length of the first optical path. Because the change in optical path length of the first optical path includes a change in optical path length of light passing through a part of the sample 5, if the sample 5 has dispersion, the influence of dispersion in the first optical path changes correspondingly. Accordingly, simply changing the air spacing between the optical devices in the second optical path with respect to the change in optical path length of the first optical path allows the optical path lengths of the first and second optical paths to become equal to each other but cannot equalize the influence of dispersion in the first and second optical paths with each other. The above-described arrangement makes it possible to change the optical thickness of the at least one dispersion adjusting device placed in the second optical path. Therefore, it is possible to adjust the dispersion in accordance with a change in dispersion influence caused by the sample 5, which results from a change in z-coordinate of the observation plane or the like. When there has been a change in influence of the dispersion in the microscope optical path, e.g. when the sample 5 has been changed for another, or when an optical device having dispersion has been newly placed in the microscope optical path, it is also possible to perform an optimal dispersion adjustment at the time of carrying out observation.

The scanning microscope may be arranged such that he depth of the observation plane in the sample 5 from the surface of the sample 5 can be adjusted by changing the optical thickness of the dispersion adjusting device. Changing the optical thickness of the dispersion adjusting device causes a change in optical path length of the second optical path and hence causes a change in z-coordinate of the observation position 6 in the sample 5, at which the first optical path has an optical path length substantially equal to that of the second optical path. If the depth of focus of the objective optical system 4 is sufficiently greater than the coherence length, the z-coordinate of the observation position 6 can be changed without substantially changing the resolution in the xy-plane. Accordingly, the depth (z-coordinate) of the observation plane in the sample 5 can be changed by changing the optical thickness of the dispersion adjusting device. As has been stated above, the dispersion adjusting device makes it possible to perform an optimal dispersion adjustment at the time of carrying out observation. Therefore, it is possible to simultaneously adjust the depth of the observation plane in the sample 5 and the dispersion, which may be changed by the depth adjustment.

The scanning microscope may be arranged so that the dispersion characteristics of the dispersion adjusting device in the wavelength region of the low-coherence light are substantially equal to the dispersion characteristics of the sample 5. If the optical thickness of the dispersion adjusting device is set at a value approximately double the depth of the observation position 6 in the sample 5 from the surface of the sample 5, the optical path length of light passing through the dispersion adjusting device and the optical path length of light passing through a part of the sample 5 become substantially equal to each other. Therefore, it is possible to substantially equalize the influence of dispersion introduced by the sample 5 and the influence of dispersion introduced by the dispersion adjusting device. Accordingly, it is possible to further facilitate the above-described simultaneous adjustment, that is, the adjustment of the depth of the observation plane and the adjustment of the dispersion, which may be changed by the depth adjustment.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF THE PREFERRED EMBODIMENTS

Some examples of the scanning microscope according to the present invention will be described below with reference to the accompanying drawings.

EXAMPLE 1

Figure 1:
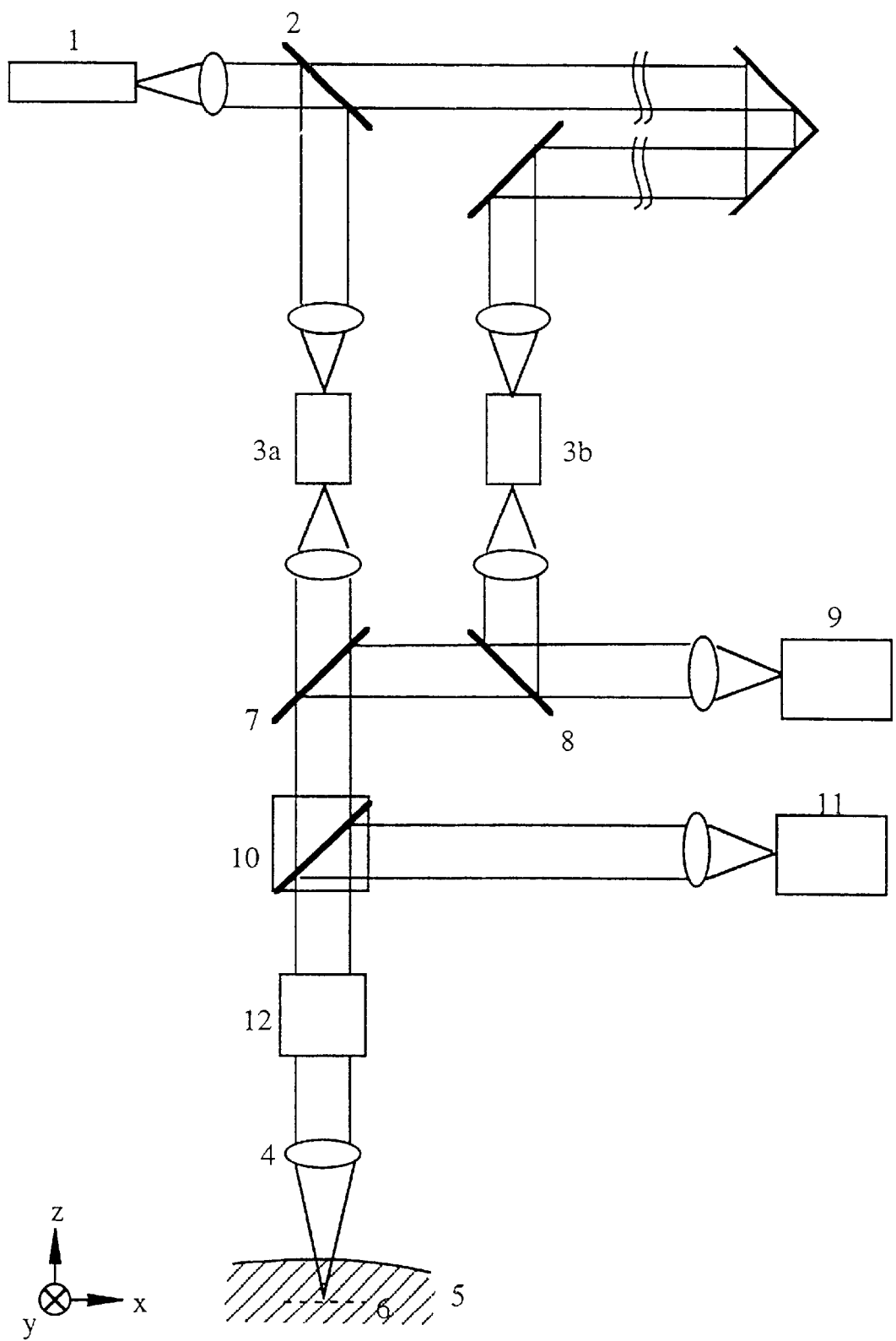
FIG. 1 is a diagram showing the arrangement of a scanning microscope according to the present invention.
Figure 2:
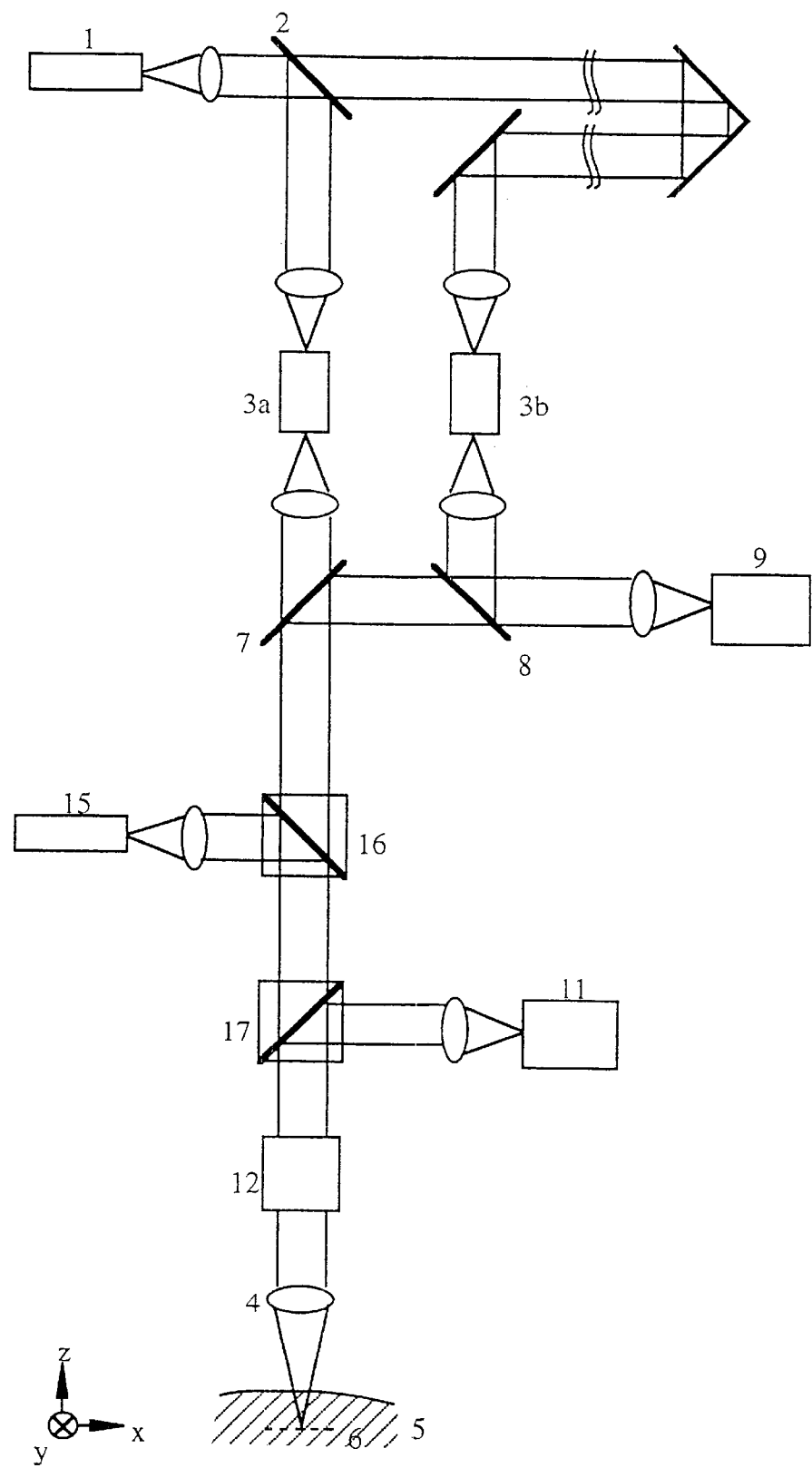
FIG. 2 is a diagram showing the arrangement of a scanning microscope according to the present invention that has a low-coherence light source and a fluorescence excitation light source.
Figure 3:
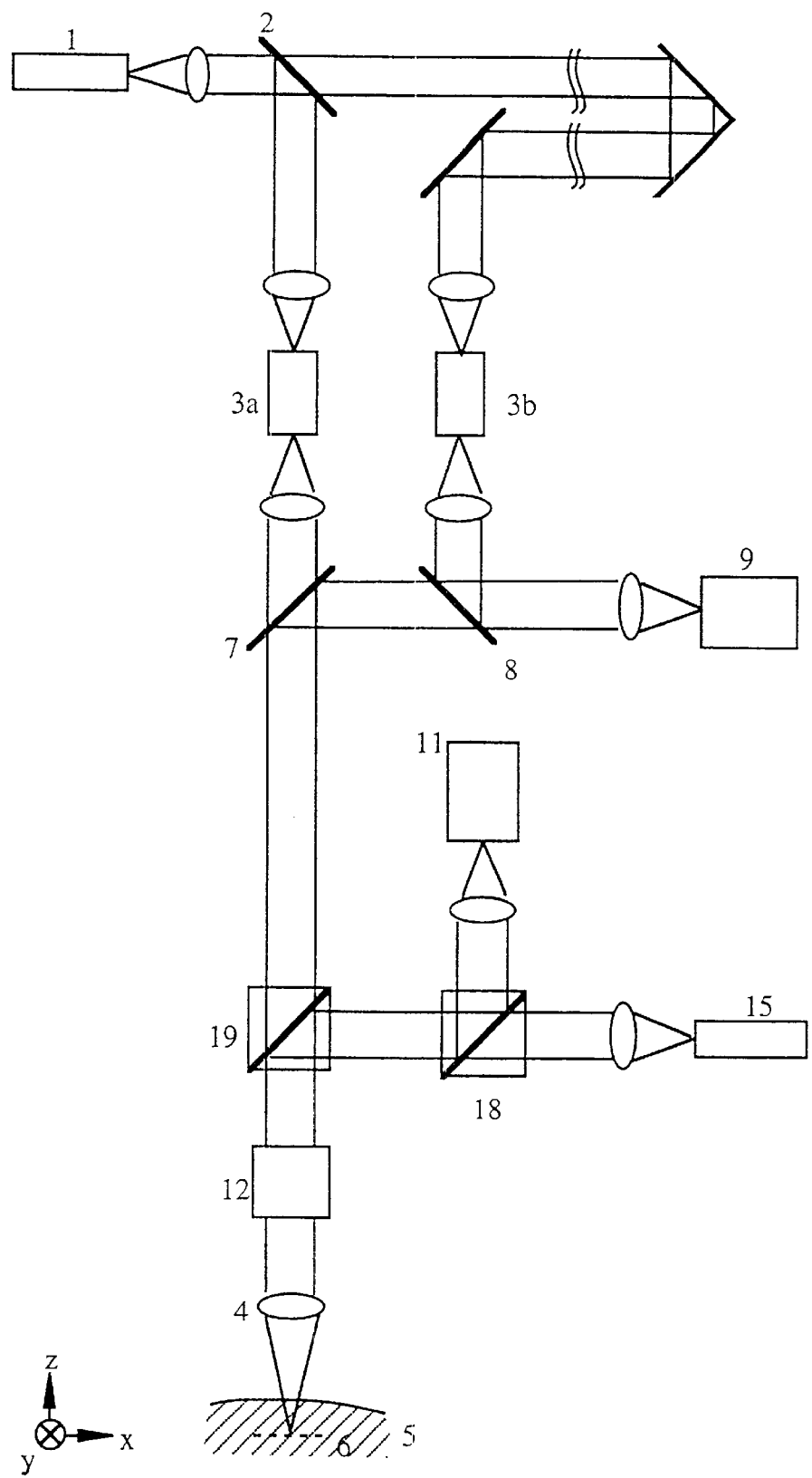
FIG. 3 is a diagram showing the arrangement of a scanning microscope in which an excitation light combining device and a fluorescence branching device are arranged to perform each other's function as well as their own functions.
Figure 4:
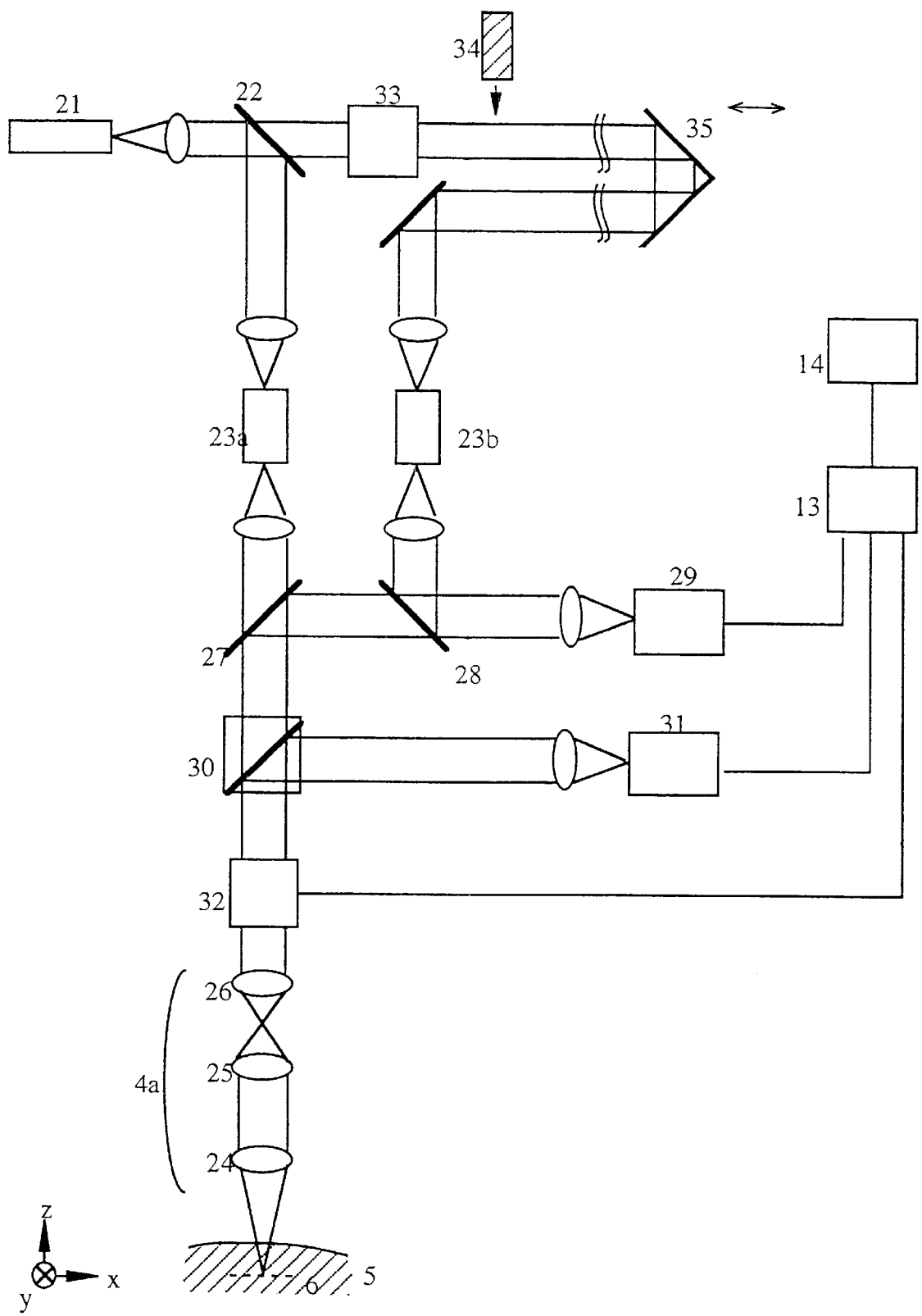
FIG. 4 is a ray path diagram of a scanning microscope according to Example 1 of the present invention.

FIG. 4 is a ray path diagram showing the arrangement of an example of the scanning microscope according to the present invention. In this example, a pulse laser is used as a low-coherence light source, and both a fluorescence image produced by two-photon excitation and a low-coherence interference image are observed simultaneously.

A low-coherence light source 21 is a pulse laser in which the center wavelength $\lambda_c$ is 850 nm and the spectral width $\Delta\lambda$ is 50 nm. The coherence length $L_c$ of the low-coherence light source 21 is given by $$L_c = \lambda_c^2/\Delta\lambda$$

Accordingly, the coherence length $L_c$ of the low-coherence light source 21 is about 14.5 $\mu$m. Light from the light source 21 is split between a first optical path and a second optical path by a beam splitter 22. The split ratio of the beam splitter 22 may be set at an appropriate value according to the intensity of light returning from the sample 5. In this example, an optical path along which light reflected by the beam splitter 22 travels is defined as a first optical path, and an optical path along which light passing through the beam splitter 22 travels is defined as a second optical path.

Figure 5:
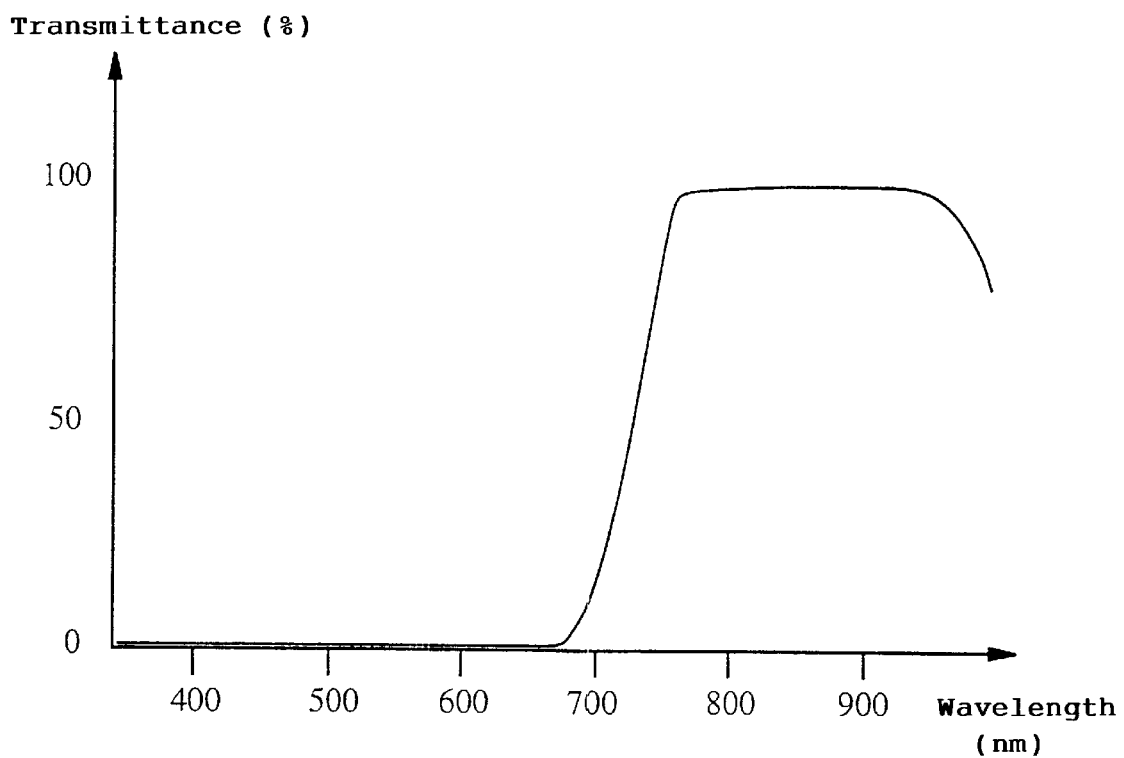
FIG. 5 is a diagram showing the spectral characteristics of a dichroic mirror in Example 1.

First, the first optical path will be described. Light reflected by the beam splitter 22 travels along the first optical path and passes through an acoustooptic device 23a having a modulation frequency of 80 MHz. Then, the light passes successively through a beam splitter 27 and a dichroic mirror 30. The dichroic mirror 30 separates low-coherence light and fluorescence produced by two-photon excitation caused by the low-coherence light. Assuming that the wavelength of fluorescence produced in this example is of the order of 500 to 600 nm, the dichroic mirror 30 has spectral characteristics as shown in FIG. 5. Light passing through the dichroic mirror 30 is passed through an xy-scanner 32 and an objective optical system 4a to scan across an area within a sample 5 in an xy-plane. The objective optical system 4a consists essentially of a pupil projection lens 26, an imaging lens 25, and an objective lens 24. Fluorescence from the sample 5 passes through the objective optical system 4a and the xy-scanner 32. Then, the fluorescence is reflected by the dichroic mirror 30 and detected by a fluorescence detecting system 31. Meanwhile, scattered light (low-coherence light) from the sample 5 passes through the objective optical system 4a and the xy-scanner 32. Then, the scattered light passes through the dichroic mirror 30 and is reflected by the beam splitter 27. The reflected light passes through a beam splitter 28 to combine with the light passing through the second optical path.

Next, the second optical path will be described. Light passing through the beam splitter 22 travels along the second optical path and passes through a dispersion adjusting device 33 (described later). Thereafter, the light is reflected by a turn-back mirror 35 and passes through an acoustooptic device 23b having a modulation frequency of 80.5 MHz. Then, the light is reflected by the beam splitter 28 to combine with the light passing through the first optical path. The turn-back mirror 35 is movable in the direction indicated by the arrow in the figure. The z-coordinate of an observation position 6 in the sample 5 at which the user wants to perform observation can be preset by adjusting the position of the turn-back mirror 35 in advance. The position of the turn-back mirror 35 is fixed while one section in the sample 5 is being observed. It should be noted that the turn-back mirror 35 may be placed in the first optical path instead of placing it in the second optical path. For example, the turn-back mirror 35 may be disposed between the beam splitter 27 and the beam splitter 28.

In the first optical path, the acoustooptic device 23a, the objective optical system 4a and the sample 5 are considered to be the main causes of dispersion. As has been stated above, it is desirable that the dispersion characteristics of the first and second optical paths in the wavelength region of the low-coherence light should be equal to each other. Therefore, the acoustooptic device 23a in the first optical path and the acoustooptic device 23b in the second optical path are formed by using acoustooptic crystals prepared to the same specifications and different only in modulation frequency. To compensate for the influence of the dispersion of the objective optical system 4a, which is present only in the first optical path, a medium (dispersion adjusting device) 33 having substantially the same dispersion characteristics as the objective optical system 4a is placed in the second optical path. As the medium 33, for example, an appropriate glass material or liquid is usable. When the sample 5 also has dispersion, a medium 34 having substantially the same dispersion characteristics as the sample 5 can be inserted into the second optical path. In this case, however, the optical path length of the second optical path may be changed by the insertion of the medium 34. Therefore, it may be necessary to slightly adjust the optical path length of the second optical path by adjusting the position of the turn-back mirror 35.

The light passing through the first optical path and the light passing through the second optical path are combined in the beam splitter 28 and detected by an interference signal detecting system 29. It is desirable that the split ratio of the beam splitter 28 should be set at an appropriate value according to the intensity of light returning from the sample 5 as in the case the beam splitter 22. The interference signal detecting system 29 detects the intensity of a light signal having a frequency of 0.5 MHz, which is the difference between the modulation frequencies of the acoustooptic devices 23a and 23b. The signal from the interference signal detecting system 29 and the signal from the fluorescence detecting system 31 are processed in a computer 13. The computer 13 also controls the xy-scanner 32 and allows an output unit 14 to display a low-coherence interference image and a fluorescence image in the xy-plane at the observation position 6 in the sample 5. The low-coherence interference image and the fluorescence image may be displayed separately or superimposed on one another.

EXAMPLE 2

Figure 6:
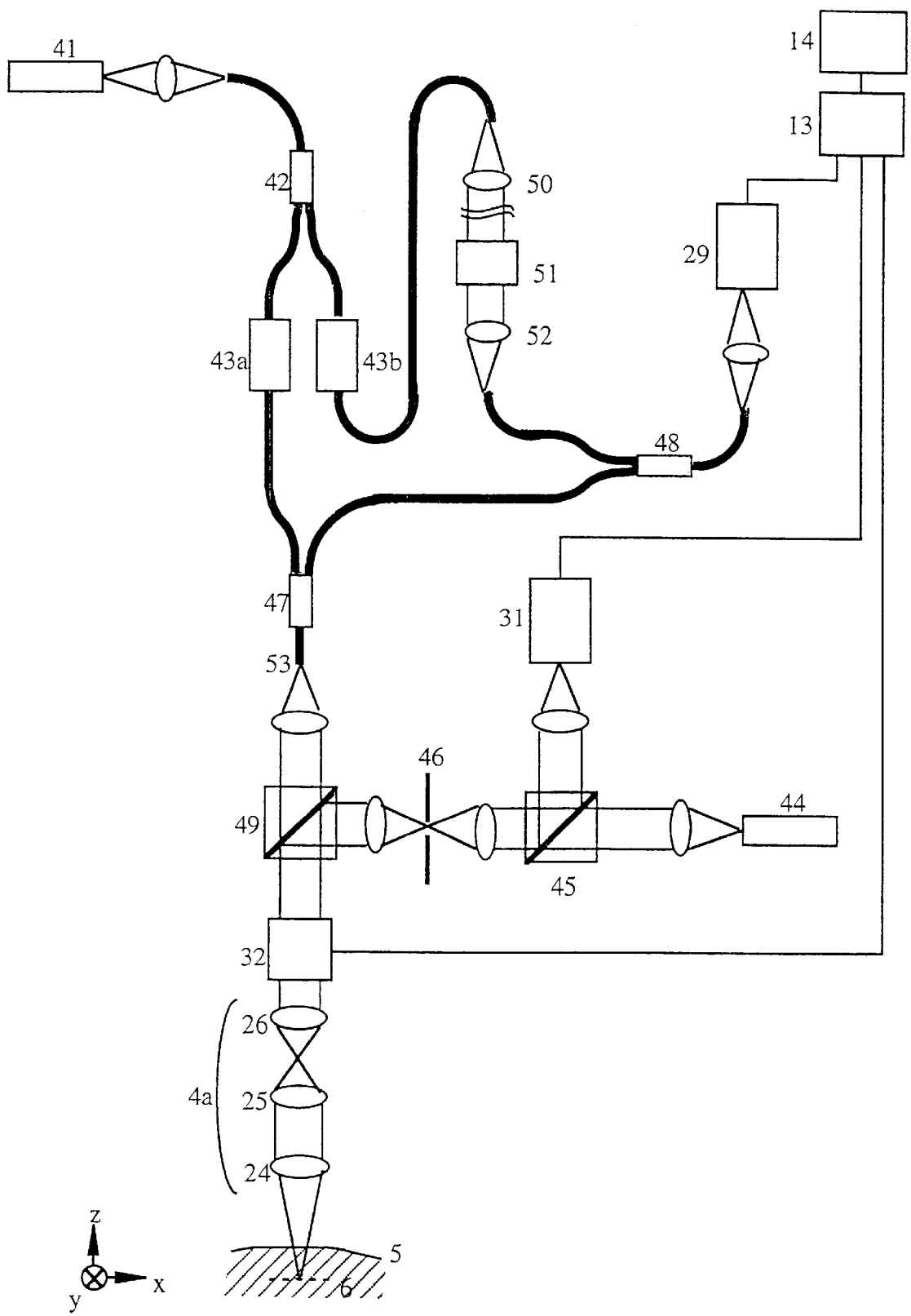
FIG. 6 is a ray path diagram of a scanning microscope according to Example 2 of the present invention.

FIG. 6 is a ray path diagram showing the arrangement of another example of the scanning microscope according to the present invention. In this example, the scanning microscope has a low-coherence light source and a fluorescence excitation light source and uses optical fibers in a part of an optical system thereof.

First, an optical system for performing low-coherence interferometric observation will be described. A low-coherence light source 41 is a fiber light source in which the center wavelength $\lambda_c$ is 1300 nm and the spectral width $\Delta\lambda$ is 50 nm. Accordingly, the coherence length $L_c$ of the low-coherence light source 41 is about 34 $\mu$m. Light from the light source 41 enters an optical fiber and is split by a fiber splitter 42. One of the split light passes through an acoustooptic device 43a, and the other passes through an acoustooptic device 43b. The split ratio of the fiber splitter 42 is appropriately set as in the case of the beam splitters 22 and 28 in Example 1. In this example, an optical path along which light passing through the acoustooptic device 43a travels is defined as a first optical path, and an optical path along which light passing through the acoustooptic device 43b travels is defined as a second optical path.

First, the first optical path will be described. Light passing through the acoustooptic device 43a, which has a modulation frequency of 80 MHz, passes through a fiber splitter 47 and further passes through a dichroic mirror 49 (described later). Then, the light passes through an xy-scanner 32 and an objective optical system 4a, thereby being applied to a sample 5. Light scattered by the sample 5 passes through the objective optical system 4a and the xy-scanner 32 and further passes through the dichroic mirror 49 and the fiber splitter 47. Then, the light is combined with light passing through the second optical path in a fiber splitter 48.

Next, the second optical path will be described. Light passing through the acoustooptic device 43b, which has a modulation frequency of 80.5 MHz, is formed into parallel rays of light through a collimator lens 50. Then, the light passes through a dispersion adjusting device 51 and enters an optical fiber through a condenser lens 52. The dispersion adjusting device 51 is a medium whereby dispersion characteristics produced in the first and second optical paths, respectively, are made substantially equal to each other. Because optical fibers are used in this example, it is desirable to take into account also the dispersion of the optical fibers when there is a large difference in optical fiber length between the first and second optical paths. Meanwhile, the distance between the collimator lens 50 and the condenser lens 52 is adjustable. Accordingly, it is possible to make an adjustment so that the optical path length of the first optical path and the optical path length of the second optical path are equal to each other with respect to an observation position 6 in the sample 5. Thus, the z-coordinate of the observation position 6 can be preset.

The light passing through the first optical path and the light passing through the second optical path are combined in the fiber splitter 48 and then detected by an interference signal detecting system 29. The interference signal detecting system 29 detects the intensity of a light signal having a frequency of 0.5 MHz, which is the difference between the modulation frequencies of the acoustooptic devices 43a and 43b.

Figure 7:
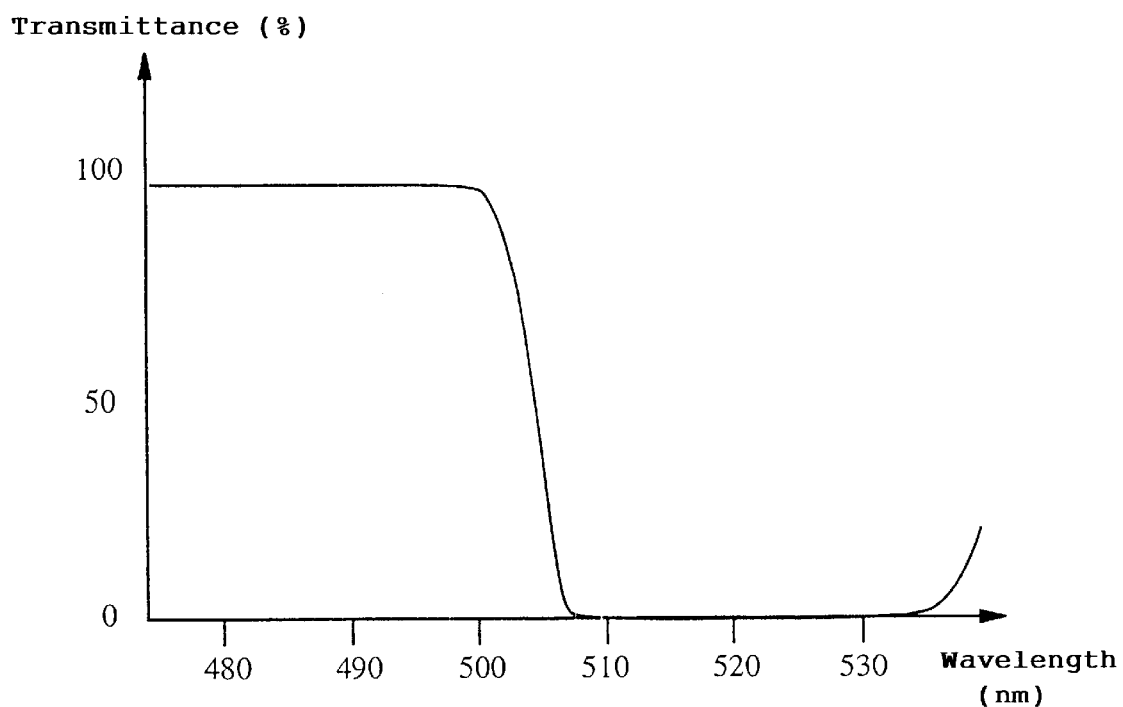
FIG. 7 is a diagram showing the spectral characteristics of one dichroic mirror in Example 2.
Figure 8:
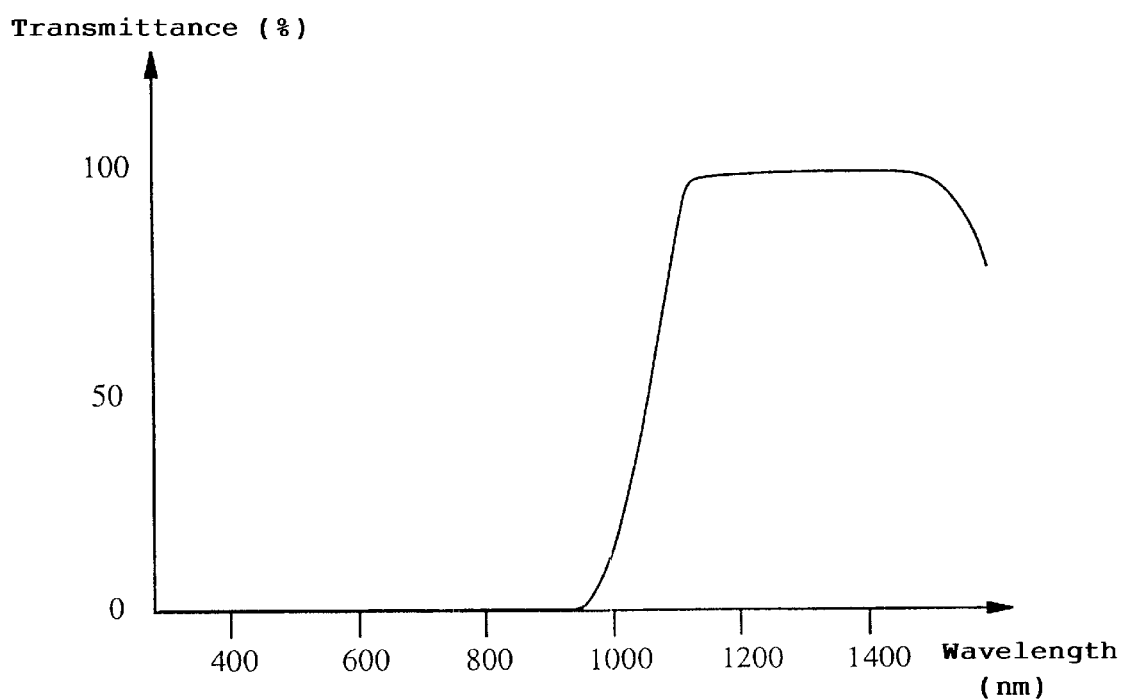
FIG. 8 is a diagram showing the spectral characteristics of the other dichroic mirror in Example 2.

Next, an optical system for performing fluorescence observation will be described. It is assumed that the fluorescence excitation light source 44 is an argon ion laser having a wavelength of 488 nm, and fluorescence emitted from the sample 5 by the excitation light from the argon ion laser has a wavelength of about 520 nm. Light from the fluorescence excitation light source 44 passes through a dichroic mirror 45 and further passes through a pinhole 46. Then, the light is reflected by the dichroic mirror 49 and applied to the sample 5 through the xy-scanner 32 and the objective optical system 4a. Fluorescence from the excited sample 5 passes through the objective optical system 4a and the xy-scanner 32 and is reflected by the dichroic mirror 49. After passing through the pinhole 46, the fluorescence is reflected by the dichroic mirror 45 and detected by a fluorescence detecting system 31. The dichroic mirror 45 separates excitation light and fluorescence from each other, and the dichroic mirror 49 separates low-coherence light and excitation light or fluorescence from each other. Accordingly, the dichroic mirrors 45 and 49 have spectral characteristics as shown in FIGS. 7 and 8, respectively.

In the scanning microscope according to this example, the fiber exit end 53 serves as a confocal pinhole in the low-coherence interferometric observation optical system, and the pinhole 46 serves as a confocal pinhole in the fluorescence observation optical system. This is useful to improve the resolution or the sectioning effect.

Further, in this example, the essential parts of the optical system for low-coherence interferometric observation are connected by optical fibers, and thus the layout of the optical devices can be arranged relatively freely. Therefore, the optical system for low-coherence interferometric observation can be readily added to an existing laser scanning fluorescence microscope.

EXAMPLE 3

Figure 9:
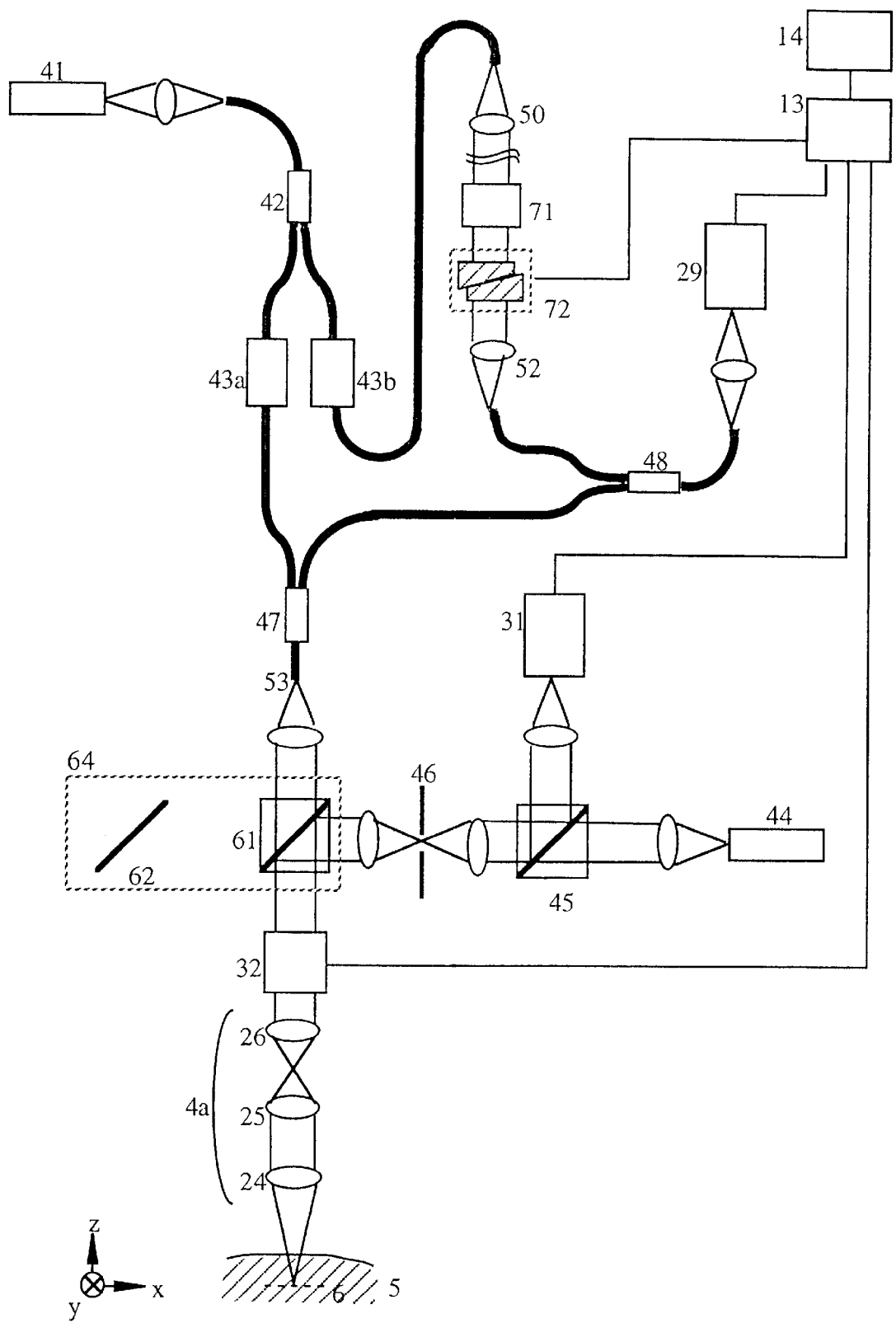
FIG. 9 is a ray path diagram of a scanning microscope according to Example 3 of the present invention.

FIG. 9 is a ray path diagram showing the arrangement of another example of the scanning microscope according to the present invention. In this example, the scanning microscope has a low-coherence light source and a fluorescence excitation light source and uses optical fibers in a part of an optical system thereof. Because the arrangement of the basic part is the same as that in Example 2, only a part in which this example differs from Example 2 will be described below.

Figure 10:
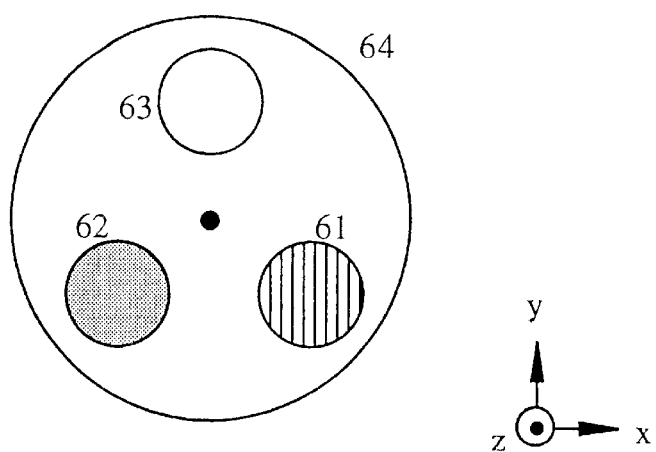
FIG. 10 is a diagram showing the arrangement of a turret in Example 3.
Figure 11:
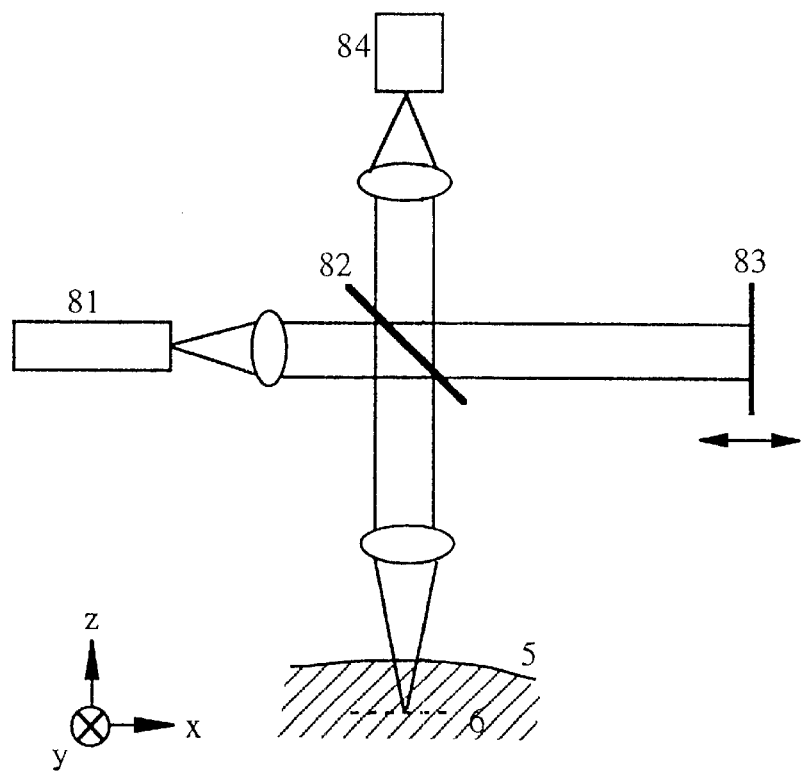
FIG. 11 is a diagram showing the arrangement of a conventional low-coherence interferometric optical system.
Figure 12:
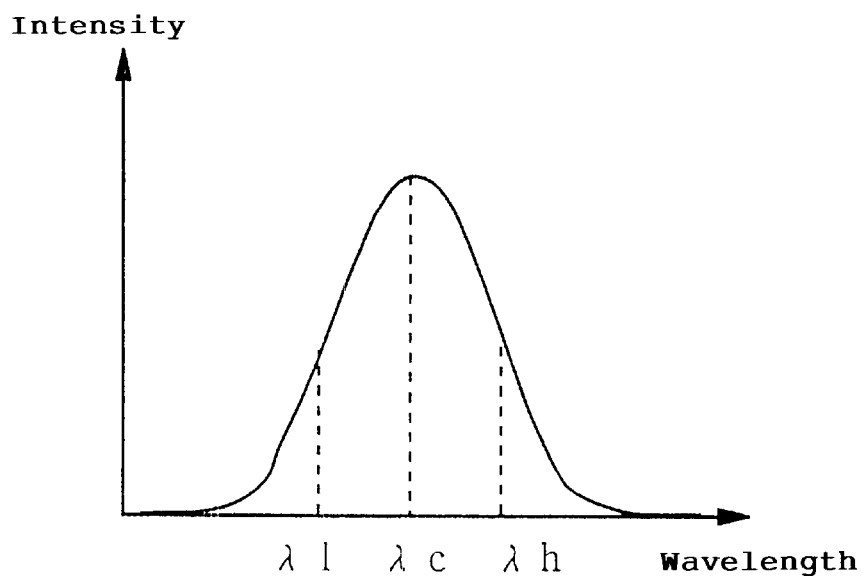
FIG. 12 is a diagram showing an example of the spectrum of a low-coherence light source.
Figure 13:
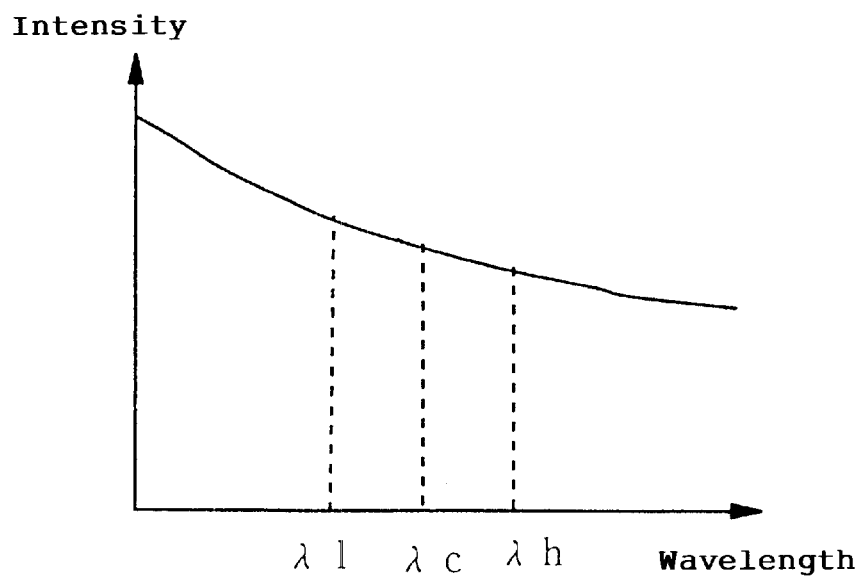
FIG. 13 is a diagram showing an example of dispersion characteristics.

In this example, the part of dichroic mirror 49 is formed from a turret 64 that allows selection of any of a dichroic mirror 61, a mirror 62, and a blank hole 63, as shown in FIG. 10. When the dichroic mirror 61 is selected, low-coherence interferometric observation and fluorescence observation can be performed simultaneously as in the case of Example 2. When the mirror 62 is selected, only fluorescence observation can be performed. When the blank hole 63 is selected, only low-coherence interferometric observation can be performed. With this arrangement, the optical paths can be readily switched from one to another to perform observation with a maximized signal light quantity, for example, when the fluorescence intensity or the intensity of scattered low-coherence light is very feeble.

Further, this example differs from Example 2 in the arrangement of the optical system disposed between the collimator lens 50 and the condenser lens 52. In this example, a dispersion adjusting device 71 and a dispersion adjusting device 72 that is controlled by the computer 13 are disposed between the collimator lens 50 and the condenser lens 52. The dispersion adjusting device 71 is a medium having dispersion characteristics substantially equal to the dispersion characteristics of the objective optical system 4a. The dispersion adjusting device 72 has dispersion characteristics substantially equal to the dispersion characteristics of the sample 5. In addition, the optical thickness of the dispersion adjusting device 72 is variable for adjustment. For example, the dispersion adjusting device 72 is arranged to allow the optical thickness to be adjusted by changing the thickness of a glass material, a liquid, etc. In FIG. 9, one of two superimposed trapezoidal prisms is displaced relative to the other, thereby changing the optical thickness of the dispersion adjusting device 72. The optical thickness of the dispersion adjusting device 72 is set at a value approximately double the depth of the observation position 6 in the sample 5 from the surface of the sample 5. Accordingly, if the optical thickness of the dispersion adjusting device 72 is changed by the computer 13, the z-coordinate of the observation position 6 in the sample 5 can be adjusted in accordance with the amount of change in optical thickness of the dispersion adjusting device 72. Because the amount of change in optical thickness of the dispersion adjusting device 72 is substantially equal to the amount of change in optical path length caused by the change in z-coordinate of the observation position 6, the dispersion adjustment made by the dispersion adjusting device 72 always optimally compensates for the influence of dispersion caused by a change in z-coordinate of the sample 5.

As will be clear from the foregoing description, the scanning microscope according to the present invention provides the following advantageous effects. When performing fluorescence observation of the inside of a thick sample or the inside of an opaque scattering sample, it is possible to simultaneously observe a fluorescence image and a low-coherence interference image in the same region of interest as that for the fluorescence observation. Moreover, it is possible to obtain both a fluorescence observation image and a low-coherence interferometric observation image within a reduced period of time.

I claim:

1. A scanning microscope comprising:
   a low-coherence light source;
   means for splitting low-coherence light from said low-coherence light source between a first optical path and a second optical path;

frequency modulating means placed in at least one of said first optical path and said second optical path to produce a frequency difference between light passing through said first optical path and light passing through said second optical path without changing an optical path length of each optical path;

an objective optical system placed in said first optical path to apply light to a sample and to collect light from said sample;

scanning means placed in said first optical path to scan said sample and the light applied by said objective optical system relative to each other in a plane perpendicular to an optical axis of said objective optical system;

means for combining together said first optical path and said second optical path;

an interference signal detecting system for detecting an interference signal having said frequency difference from the combined light;

fluorescence branching means for branching fluorescence from said sample excited by said low-coherence light; and a fluorescence detecting system for detecting the fluorescence branched by said fluorescence branching means.

2. A scanning microscope according to claim 1, wherein said low-coherence light source is a pulse laser.

3. A scanning microscope according to claim 1, wherein said frequency modulating means is an acoustooptic device.

4. A scanning microscope according to claim 3, wherein said low-coherence light source is a pulse laser.

5. A scanning microscope according to claim 3, wherein said fluorescence branching means is a dichroic mirror.

6. A scanning microscope according to claim 5, wherein at least one of said interference signal detecting system and said fluorescence detecting system is a confocal system.

7. A scanning microscope according to claim 1, wherein at least one of said first optical path and said second optical path is provided with at least one dispersion adjusting means for substantially equalizing dispersion characteristics produced in said first optical path and said second optical path, respectively, in a wavelength region of said low-coherence light.

8. A scanning microscope according to claim 7, wherein said at least one dispersion adjusting means provided in said second optical path is variable in optical thickness.

9. A scanning microscope according to claim 8, wherein a depth of an observation plane in said sample from a sample surface is adjustable by changing the optical thickness of said dispersion adjusting means.

10. A scanning microscope according to claim 9, wherein dispersion characteristics of said dispersion adjusting means in the wavelength region of said low-coherence light are substantially equal to dispersion characteristics of said sample.

11. A scanning microscope according to claim 3, wherein at least one of said first optical path and said second optical path is provided with at least one dispersion adjusting means for substantially equalizing dispersion characteristics produced in said first optical path and said second optical path, respectively, in a wavelength region of said low-coherence light.

12. A scanning microscope comprising:
a low-coherence light source;
means for splitting low-coherence light from said low-coherence light source between a first optical path and a second optical path;

frequency modulating means placed in at least one of said first optical path and said second optical path to produce a frequency difference between light passing through said first optical path and light passing through said second optical path without changing an optical path length of each optical path;

an objective optical system placed in said first optical path to apply light to a sample and to collect light from said sample;

scanning means placed in said first optical path to scan said sample and the light applied by said objective optical system relative to each other in a plane perpendicular to an optical axis of said objective optical system;

means for combining together said first optical path and said second optical path;

an interference signal detecting system for detecting an interference signal having said frequency difference from the combined light;

a fluorescence excitation light source;

excitation light combining means for combining together excitation light from said fluorescence excitation light source and said low-coherence light in said first optical path;

fluorescence branching means for branching fluorescence from said sample excited by said excitation light; and a fluorescence detecting system for detecting the fluorescence branched by said fluorescence branching means.

13. A scanning microscope according to claim 12, wherein said excitation light combining means and said fluorescence branching means are formed from at least two dichroic mirrors.

14. A scanning microscope according to claim 12, wherein one of said excitation light combining means and said fluorescence branching means is a dichroic mirror, and the other is a mirror capable of switching between optical paths.

15. A scanning microscope according to claim 12, wherein at least one of said interference signal detecting system and said fluorescence detecting system is a confocal system.

16. A scanning microscope according to claim 12, wherein said frequency modulating means is an acoustooptic device.

17. A scanning microscope according to claim 16, wherein at least one of said interference signal detecting system and said fluorescence detecting system is a confocal system.

18. A scanning microscope according to claim 17, wherein said excitation light combining means and said fluorescence branching means are formed from at least two dichroic mirrors.

19. A scanning microscope according to claim 17, wherein one of said excitation light combining means and said fluorescence branching means is a dichroic mirror, and the other is a mirror capable of switching between optical paths.

20. A scanning microscope according to claim 12, wherein at least one of said first optical path and said second optical path is provided with at least one dispersion adjusting means for substantially equalizing dispersion characteristics produced in said first optical path and said second optical path, respectively, in a wavelength region of said low-coherence light.

21. A scanning microscope according to claim 20, wherein said at least one dispersion adjusting means provided in said second optical path is variable in optical thickness.

22. A scanning microscope according to claim 21, wherein a depth of an observation plane in said sample from a sample surface is adjustable by changing the optical thickness of said dispersion adjusting means.

23. A scanning microscope according to claim 22, wherein dispersion characteristics of said dispersion adjusting means in the wavelength region of said low-coherence light are substantially equal to dispersion characteristics of said sample.

24. A scanning microscope according to claim 16, wherein at least one of said first optical path and said second optical path is provided with at least one dispersion adjusting means for substantially equalizing dispersion characteristics produced in said first optical path and said second optical path, respectively, in a wavelength region of said low-coherence light.

* * * * *